United States Patent
Voth et al.

(10) Patent No.: US 8,828,290 B2
(45) Date of Patent: Sep. 9, 2014

(54) BLOW MOULD CAPABLE OF BEING STERILIZED

(75) Inventors: Klaus Voth, Obertraubling (DE); Oliver Martini, Konolfingen (CH); Ulrich Lappe, Regensburg (DE); Juergen Soellner, Beratzhausen (DE); Frank Winzinger, Regensburg (DE); Josef Hausladen, Woerth/Donau (DE)

(73) Assignee: Krones AG, Neutraubling (DE)

( * ) Notice: Subject to any disclaimer, the term of this patent is extended or adjusted under 35 U.S.C. 154(b) by 370 days.

(21) Appl. No.: 13/110,511

(22) Filed: May 18, 2011

(65) Prior Publication Data

US 2011/0311675 A1 Dec. 22, 2011

(30) Foreign Application Priority Data

May 20, 2010 (DE) .......................... 10 2010 022 131

(51) Int. Cl.
| | |
|---|---|
| B29C 49/36 | (2006.01) |
| B29C 49/42 | (2006.01) |
| B29C 33/72 | (2006.01) |
| A61L 2/04 | (2006.01) |
| B29C 49/48 | (2006.01) |
| A61L 2/10 | (2006.01) |
| B29C 49/12 | (2006.01) |
| B29C 49/46 | (2006.01) |

(52) U.S. Cl.
CPC ..... *B29C 49/4252* (2013.01); *B29C 2049/4892* (2013.01); *A61L 2/10* (2013.01); *B29C 2049/4838* (2013.01); *B29C 49/12* (2013.01); *B29C 49/42* (2013.01); *B29C 2049/4697* (2013.01); *B29C 49/482* (2013.01); *A61L 2/04* (2013.01)

USPC ............ 264/39; 264/538; 264/543; 425/522; 425/526; 425/540

(58) Field of Classification Search
CPC B29C 49/36; B29C 49/4252; B29C 49/4823; B29C 33/72
USPC ............ 264/39, 538, 543; 425/522, 526, 540
See application file for complete search history.

(56) References Cited

U.S. PATENT DOCUMENTS 5,248,533 A * 9/1993 Sugiura et al. ................ 264/535
6,773,656 B2 * 8/2004 Kannari et al. ............... 264/515

(Continued)

FOREIGN PATENT DOCUMENTS

DE 10064167 A1 * 7/2002
DE 102007017938 A1 * 10/2008

(Continued)

OTHER PUBLICATIONS

Partial machine translation of DE10064167A1 dated Jul. 2002 obtained from the espace.net website.*

(Continued)

*Primary Examiner* — Robert B Davis
(74) *Attorney, Agent, or Firm* — Novak Druce Connolly Bove + Quigg LLP

(57) ABSTRACT

A method of treating devices of a plant for producing plastics material containers may include the steps of selection of at least one treatment device, acting upon the treatment device with a sterilization temperature in order to sterilize the treatment device, supplying at least one plastics material pre-form to the treatment device, shaping the plastics material pre-form to form a plastics material container, and removal of the at least one plastics material container from the treatment device.

18 Claims, 2 Drawing Sheets

(56) References Cited

U.S. PATENT DOCUMENTS

| | | |
|---|---|---|
| 8,092,757 B2 | 1/2012 | Adriansens et al. |
| 8,231,823 B2 | 7/2012 | Humele et al. |
| 2010/0089009 A1* | 4/2010 | Till .................................. 53/452 |
| 2010/0303946 A1* | 12/2010 | Voth ............................... 425/226 |
| 2011/0133370 A1 | 6/2011 | Engelhard et al. |
| 2011/0272861 A1 | 11/2011 | Humele |

FOREIGN PATENT DOCUMENTS

| | | |
|---|---|---|
| DE | 10 2008 030 156 A1 | 12/2009 |
| DE | 10 2008 038 143 A1 | 2/2010 |
| DE | 10 2008 056 346 A1 | 5/2010 |
| EP | 1 896 245 B1 | 3/2008 |
| JP | 56013142 A * | 2/1981 |
| JP | 03049926 A * | 3/1991 |
| WO | 2007/131701 A2 | 11/2007 |

OTHER PUBLICATIONS

Partial machine translation of DE102007017938A1 dated Oct. 2008 obtained from the espace.net website.*

German Search Report dated Jul. 29, 2011, issued in counterpart German Application No. 10 2010 022 131.7.

* cited by examiner

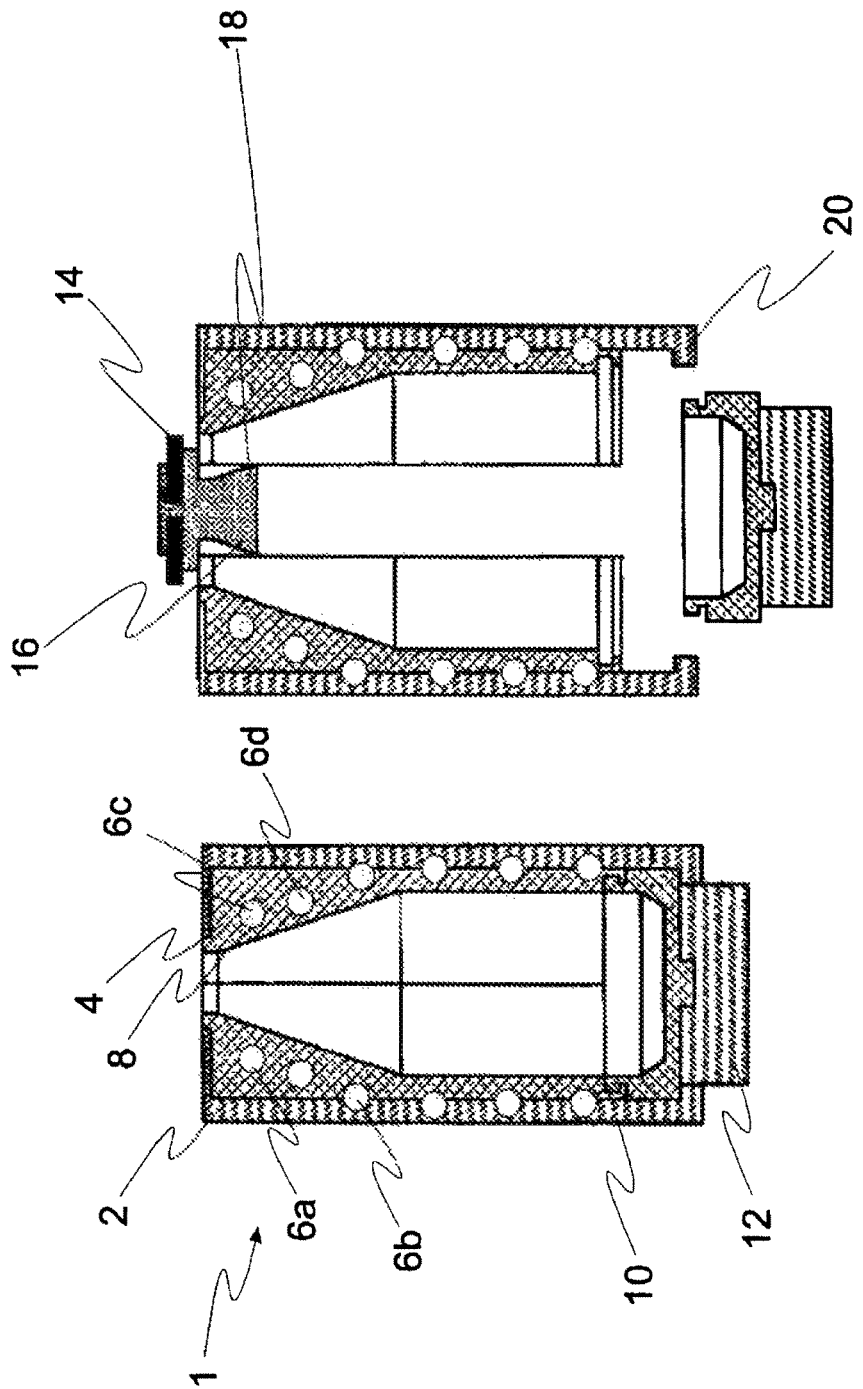

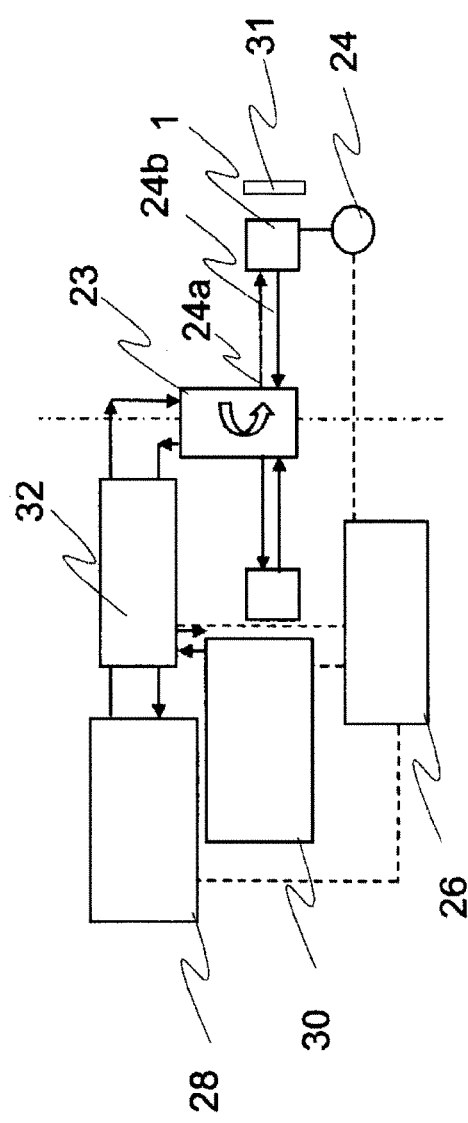
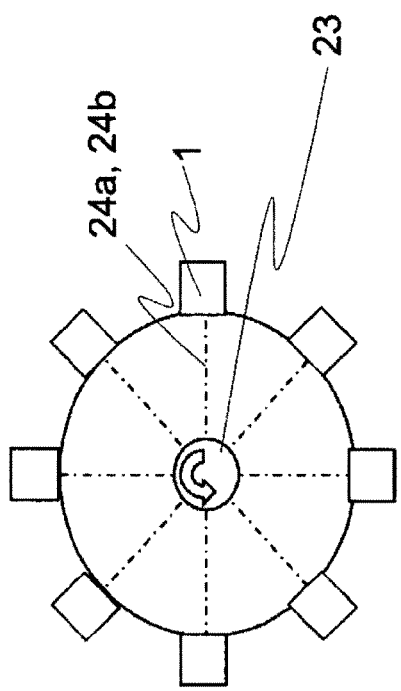
Fig. 3
Fig. 4

BLOW MOULD CAPABLE OF BEING STERILIZED

CROSS-REFERENCE TO RELATED APPLICATION

This application claims the benefit of priority of German Patent Application No. 10 2010 022 131.7, filed May 20, 2010, pursuant to 35 U.S.C. 119(a)-(d), the disclosure of which is incorporated herein by reference.

TECHNICAL FIELD

The present disclosure relates to a method of sterilizing a treatment device in a plant for producing plastics material containers, to a blow mould for shaping plastics material pre-forms into containers, and to the use of a tempering medium for tempering a blow mould. Blow moulds according to the present disclosure are used in a particularly preferred manner for shaping pre-forms or plastics material pre-forms into containers, such as for example PET bottles, canisters, barrels and the like.

BACKGROUND

In accordance with modern requirements with respect to the sterility of filling plants, in particular aseptic treatment plants, it is necessary for the containers to be provided as far as possible in a sterile environment during the entire treatment process. It is therefore necessary not only to keep the interior of the containers or the preforms sterile or germ-free but likewise to keep the exterior of the pre-forms or the containers sterile or germ-free, so that a transfer of bacteria, viruses, germs or the like present on the outside of the containers cannot take place in the region of the interior of the containers or the pre-forms and so contact of the filled material with bacteria, viruses, germs and/or the like is prevented.

It may be desirable therefore to ensure that, even during the shaping of a pre-form into a container, as few germs, bacteria, viruses or the like as possible can penetrate into the interior or into the region of the opening of a container during the shaping of a plastics material pre-form into a container.

SUMMARY

According to various aspects of the disclosure, the desired feature stated above is attained by a method of treating devices of a plant for the production of plastics material containers which comprises the following steps. It may be desirable for the aforesaid plant to be a plant which has at least one clean room.

The method steps set out below are in some aspects carried out in exactly the sequence specified below, in which case it is likewise possible for deviations from the pattern reproduced below to be feasible or for individual method steps to overlap.

In this way, in a first step it may be desirable for the selection of at least one treatment device to be carried out, which in particular is a blow mould which in some aspects is arranged at least for a time in a clean room and which in some aspects encloses at least for a time the plastics material container at least in part or is suitable for receiving or enclosing a plastics material pre-form and/or a container.

"Enclosing" is to be taken to mean, in particular, also a brief framing or surrounding of the plastics material pre-form, in part with and in part without direct contact of the pre-form, by one or more treatment devices.

In a second step the treatment device is in some aspects acted upon with a sterilization temperature in order to sterilize the treatment device. After that, it may be desirable for setting of a treatment temperature to be carried out, which is necessary during the treatment steps, i.e. the shaping of a plurality of pre-forms into plastics material containers, in particular into plastic bottles.

In accordance with the optional step of setting a treatment temperature, it is preferable for at least one plastics material pre-form to be supplied to the treatment device, in which in a further step the shaping of the plastics material pre-form to form a plastics material container is carried out. After the shaping is completed, it is particularly preferable for the plastics material container to be removed from the treatment device.

It is particularly preferable for a pressure, which is higher than the ambient temperature, to be present in the clean room. In addition, the treatment device is in some aspects arranged between a conveying device for pre-forms and a filling means. It may be advantageous for at least one conveying device for conveying the pre-forms and/or the containers to be arranged in the clean room.

The present disclosure may be advantageous since sterilization of the plant is possible before the operation steps, in particular the shaping of pre-forms or the production of containers. As a result, it is possible to achieve a reduction in germs to the point of absolute sterility in the entirety of the blowing stations or blow moulds fitted in a corresponding blowing moulding machine.

It may be preferable in some aspects for the plant, in particular the treatment device, to be dried after the completion of the operating steps or at the end of production and/or during pauses in production. This may be necessary for example if the blowing station or the blow mould is operated cooled (i.e. for example at room temperature) during the production operation, since depending upon environmental conditions this leads to precipitation and condensation water is formed in the respective blowing station or blow mould. It is known that at locations with moisture there is a high risk of the presence of germs and an increase in germs. It may therefore be preferable in some aspects for the occurrence and/or the accumulation of condensation water during the production operation of the stretch blowing station to be prevented. This is in some aspects carried out by tempering the treatment device, in particular by heating to a temperature at which the liquid, such as for example the condensation liquid is evaporated in the treatment plant. In the case of water this is possible at 1 bar for example at a temperature of 100° C., so as to ensure evaporation of the condensation water physically.

In a further exemplary embodiment of the present disclosure at least one tempering medium is provided which is in some aspects permanently connected in a thermal manner to the treatment device and by which the treatment device is tempered or is capable of being tempered at the sterilization temperature.

In this case the tempering medium can be designed for example in the form of an electrical heating device which has heating coils for example. It is likewise possible for the individual blow mould bodies to form heating resistors which are heated by electricity being passed through. In this case the tempering medium is formed by the contacts or the electrical terminals. The temperature is in some aspects supplied at least on the surface of the blow mould and, in some aspects, the inner surface of the blow mould. This is carried out for example by thermal conduction and/or thermal radiation.

It is thus likewise possible for one or more radiant heaters to be introduced into the halves of the blow mould or between the halves of the blow mould. Radiant heaters of this type can be designed for example in the form of plates or rod-shaped radiant heaters. It is additionally possible for radiant heaters to be provided in order to act upon the blow mould or the parts of the blow mould in the open or closed state with heat radiation. The halves of the blow mould can thus be arranged in the opened state between radiant heaters and can be acted upon with heat.

In addition, it is conceivable for a heat transfer fluid to bring the blowing station or the blow mould or one of the parts of the blow mould to a pre-determined temperature by way of, in some aspects, a closed circuit. The heat transfer fluid is in some aspects supplied to the individual parts of the blow mould by way of a duct system.

This embodiment may be advantageous since for example the necessary sterilization temperature, the speed of the heating, the duration of the heating and/or the like is capable of being set or regulated.

In general the expression "tempering" is understood as being the supply of heat, in particular for heating the blow mould or the parts of the blow mould.

In a further exemplary embodiment of the present disclosure a fluid tempered by the tempering medium flows around and/or through the treatment device at least locally. In this case it is conceivable for a duct or a plurality of ducts to be formed inside one or both of the parts of the blow mould. In addition, it is conceivable for a fluid communication from one part of the blow mould to the other part of the blow mould or a further part of the blow mould to be possible. In this way, for example, the fluid is capable of being supplied to and removed from the two parts of the blow mould or of only being supplied to one part of the blow mould and of being removed from the other one, or the fluid can be supplied to one part of the blow mould and can be removed from it, in which case the fluid is conveyed or is capable of being conveyed through both or a plurality (or all) of the parts of the blow mould. It is thus evident that various parts of the blow mould are capable of being heated in the same way or in different ways.

For the simple distribution of the heat in all the components which are to be sterilized, these components are in some aspects produced from metal on account of good thermal conductivity, aluminium materials being preferred in some aspects on account of their high coefficient of thermal conductivity. It is likewise possible, however, for steel and high-grade steel materials or similar materials to be used. Alternatively, a combination of different materials, such as for example aluminium reinforced with one or more further metals, is also possible in the case of these components.

It may be desirable for a fluid, which has already been used or will be subsequently used as an operating fluid, i.e. for example for the heating, operation, and/or cooling of further devices of the plant, to be supplied to the blow mould through the tempering medium.

An alternative possibility of implementing the described heating of the blowing station or the blow mould lies in the use of an additional duct system which is to be provided only for this heating and which allows the use of systems (such as for example heating devices) and fluids other than those provided for tempering during the production or during the operating step. The supply of heating water, superheated water, or superheated steam for example is particularly suitable. In certain cases it is likewise possible for a single duct system to be operated in a switchable manner with the various fluids for the production and sterilization.

This embodiment may be advantageous since the blow mould or the parts of the blow mould is or are capable of being heated in a defined manner, and the exhaust heat of further devices associated with the plant and/or a special heating by means of a tempering medium is possible.

In a further exemplary embodiment of the present disclosure the fluid consists at least in part of a water/glycol mixture, thermal oil, water, and/or the like. It is likewise possible, however, as already mentioned above, for a medium in the form of a vapour, such as for example steam or superheated steam to be used as the fluid.

This embodiment may be advantageous since a plurality of different fluids are capable of being used for the transmission of heat to the blow mould or to the parts of the blow mould. As a result, depending upon requirements, the most suitable fluids can be selected in accordance with the cost, the process pattern, ecological aspects or the like in each case.

In a further exemplary embodiment of the present disclosure the treatment device is tempered to a sterilization temperature of at least 60° C., in some aspects 100° C., and in still further aspects more than 121° C., in which case the sterilization temperature is in some aspects achieved or is capable of being achieved by electrical heating and/or by electromagnetic heating, for example, by means of induction. It may be desirable for the sterilization temperature thus to be produced by at least one tempering medium associated with the blow mould or a heating device, such as for example at least one heating coil and/or at least one coil.

The temperatures specified above are in some aspects provided in a pressure range of the medium or the environment of the blow mould of from 0.2 bar to 50 bar and, in some aspects, at a pressure of between approximately 1 bar and approximately 15 bar, in which case it is also possible for the sterilization temperature to assume different values or values adapted to the respective pressure in a manner dependent upon the given pressures. In this case it is possible, for example, in the case of low pressures, for a sterilization of the blow mould likewise to be capable of being carried out at a relatively low temperature.

In a further exemplary embodiment of the present disclosure the treatment device is tempered for at least 10 minutes, in some aspects at least 20 minutes and, in still further aspects, at least 30 minutes. In this case it is also possible, however, for the treatment device to be tempered for a considerably shorter time, i.e. for example for one minute or three minutes.

It may be desirable for the time phase specified above to describe in each case the time between the closing and the opening of the blow mould, in which case it is also possible for only the time in which an active heating of the blow mould is carried out to be regarded as the tempering time.

A reduction in germs to the point of absolute sterility is in some aspects carried out on one of the blowing stations or blow moulds or on all of the blowing stations or blow moulds fitted in the corresponding blow moulding machine and thus in some aspects by heating the station or blow mould before the production operation to the temperatures already specified. In the case of a lower requirement for a reduction in germs a good effect can be achieved even starting from a temperature of approximately 50° C. or ≥60° C.

In a further exemplary embodiment of the present disclosure the treatment device is opened after the sterilization of the blow mould in order to supply the containers. In this way, the blow mould is in some aspects closed during the sterilization, but it is likewise possible for the blow mould to be opened in part or completely during the sterilization. It may be desirable for the stretch rod to be introduced into the blow mould or into the cavity formed by the parts of the blow mould or to close it in some aspects at least in part during the sterilization or in the sterilization phase, it being desirable for no pre-form or container to be arranged in the treatment device during the sterilization.

This embodiment may be advantageous since the sterilization is in some aspects carried out when the blow mould is at least closed in part or closed completely, as a result of which the heat builds up in the region of the inner surface of the blow mould and tempering is capable of being carried out in an efficient manner.

In a further exemplary embodiment of the present disclosure at least one disinfectant is supplied to the treatment device before and/or during the stressing with the sterilization temperature, in particular to the inner surface of the blow mould. In this case it is possible for supply devices, by means of which the disinfectant is capable of being supplied in a liquid and/or gaseous state, to be formed in the vicinity of the blow mould or in the individual parts of the blow mould. In this case the disinfectant can be supplied heated, i.e. at a temperature greater than or equal to the sterilization temperature, or cold, i.e. at a temperature below the sterilization temperature. It may be desirable for the disinfectant to be supplied automatically, in some aspects in a manner dependent upon defined time or temperature values or the like. It is likewise possible, however, for the disinfectant to be supplied or to be capable of being supplied to the treatment device by means of a dispenser device and thus manually.

This embodiment may be advantageous since in particular as a result of the evaporation of the disinfectant during the heating procedure or during the tempering of the blow mould the evaporation of the disinfectant and/or the contact of the disinfectant with the germs assists the reduction in the germs to a considerable degree.

The present disclosure likewise relates to a blow mould for shaping pre-forms in containers. The blow mould comprises at least one first part of a blow mould wall and one second part of a blow mould wall movable with respect to the first part and with one inner surface and one outer surface in each case, a negative container shape being formed by the inner surface at least locally and the parts of the blow mould wall being capable of being coupled to each other by means of a coupling device in order to produce a closed state. According to the disclosure a tempering medium for tempering the blow mould at a sterilization temperature is arranged at least in the vicinity of a part of the blow mould wall at least locally.

In addition, it may be desirable for a control device to be provided which is designed in such a way that a sterilization or the temperature stressing of the blow mould is carried out substantially outside and in some aspects completely outside the working operation. The working operation in some aspects describes the phase in which a shaping of a plurality of pre-forms into containers is carried out in succession with the same blow mould, it being possible for a plurality of blow moulds to be used in parallel and/or one after the other. It thus may be desirable for a control apparatus to be present which is designed in order to control the tempering medium for tempering the blow mould, in which case the blow mould is brought or is capable of being brought to a specified sterilization temperature outside the actual operation.

It may be desirable for at least one blow mould, one blowing nozzle, one stretch rod, one base mould and/or one clamp arranged on the mould carrier to be selected as a treatment device by the control device and/or a further data-processing unit or input unit for taking up the pre-form from a transfer device for the subsequent sterilization.

In addition, the present disclosure relates to the use of a tempering medium for tempering a blow mould of a container treatment plant at a sterilization temperature.

At this point it should be further pointed out that all the features disclosed in the application documents advantageously further develop blow moulds according to the category or known from the prior art either individually or in combination with one another.

BRIEF DESCRIPTION OF THE DRAWINGS

Further advantages, aims and characteristics of the present disclosure are explained with reference to the following description of the accompanying drawings in which blow moulds for shaping plastics material pre-forms into containers are illustrated by way of example. Components of the blow moulds which correspond at least substantially with respect to their function in the figures can be designated with the same reference numbers in this case, it being unnecessary for these components to be numbered or explained in all the figures. In the drawings FIG. 1 shows a blow mould with a tempering device in a first, closed state;

FIG. 2 shows a blow mould with a tempering device in a second, opened state;

FIG. 3 is a diagrammatic illustration of an attachment of one or more tempering media to a blowing station, and FIG. 4 is a two-dimensional illustration of a rotary blowing station.

DETAILED DESCRIPTION

FIG. 1 shows a blow mould 1 which consists of a first blow mould part 2 and a second blow mould part 4. On one side the blow mould 1 is closed off by a base element and/or lid element 12. The blow mould 1 has tempering media 6a-6d in each case in the first blow mould part 2 and the second blow mould part 4. In this case the tempering media 6a-6d can be provided in any desired number or can form only one or in each case only one tempering medium and can be connected to one another in terms of their operation in each case. It is particularly preferable in some aspects for a fluid exchange between the tempering media 6a, 6b or 6a, d or 6a, 6c to be possible. The tempering media 6a-6d may be advantageously arranged in a wall region between the inner surface 8 and the outer surface 10 of the blow mould 1. It is additionally possible for the tempering media 6a-6d likewise to extend locally on the outer surface 10 of the blow mould 1 or one or both of the blow mould parts 2. It is likewise conceivable, of course, for the tempering media 6a-6d to be arranged or provided on the base element or lid element 12. It is preferable in some aspects for the tempering media 6a-6d to be designed in the form of an electrical resistance heater and, in some aspects, in the form of a fluid heater having at least one duct, the elements designated with the references 6a-6d being ducts or portions of one or more ducts shown in a cross-sectional illustration. It is also possible for a blowing nozzle, a stretch rod and/or a clamp arranged on the mould carrier in order to take up the pre-form from a transfer device during a sterilization of this type to be jointly included, and this can mean for example that it is not possible for individual or all of the specified elements to be sterilized in part or completely.

In contrast to FIG. 1, FIG. 2 does not show a closed state, but an opened state of the blow mould 1. In addition, it is evident from this illustration that a positioning device 14, such as for example a gripping clamp, is provided in order to move a holding element 18, on which an engagement element 16 is formed, into the interior of the blow mould 1 or between the first blow mould part 2 and the second blow mould part 4. The reference number 20 designates a coupling device 20.

The coupling device 20 can be designed in such a way that the blow mould parts 2, 4 are coupled or are capable of being coupled to each other in a closed state for example by positive locking, magnetic field locking and/or friction locking.

FIG. 3 is a diagrammatic illustration of possible communication paths in the framework of tempering the blow mould 1 between necessary and/or optional devices. Communication paths which are not described but which are illustrated for example describe a fluid transfer, a data exchange and/or signal exchange, an energy exchange or the like, in which case the communication can take place in both directions or only in one direction in each case.

The blow moulds 1 are connected in a communicating manner to a rotary medium distributor 23 by way of communication paths 24a, 24b. The communication paths 24a, 24b are necessary as soon as a tempering of the blow mould 1 takes place by means of at least one operating fluid or heat transfer fluid, since the tempered fluid has to be capable of being supplied to the blow mould 1. It is possible, however, for additional or alternative communication paths to be provided.

It is additionally possible for electrical or optical heating devices for tempering the blow moulds 1 to be provided or to be capable of being provided in the region of the respective blow mould 1. In this way, it is conceivable, for example, for tempering by means of a resistance heater 31 or radiation 31, in particular an infrared and/or UV radiation, to take place alternatively or optionally to the use of fluid tempering media 28, 30.

The reference number 24 designates a sensor which can be optionally provided and by means of which for example checking of nominal values of the temperature and/or of the duration of the temperature and/or monitoring of the contamination is capable of being carried out. It is particularly preferred in some aspects for the sensor 24 to be connected in a communicating manner to a machine control means 26 or in a manner exchanging data or signals. The machine control means 26 is used in some aspects to control at least one tempering medium 28 which in some aspects conveys operating fluid of further devices, which are in some aspects at least at the desired sterilization temperature, to the rotary medium distributor 23. It should be pointed out in this case that a linear distributor can likewise be provided instead of a rotary medium distributor 23.

The reference number 30 designates a special tempering medium which is capable of being provided alternatively or optionally to the tempering medium 28 and/or to an electrical or optical heating or tempering. In the case of two tempering media 28, 30 or still further tempering media 31, it is particularly preferred in some aspects for a regulating unit, in particular a group of switching valves 32, to be provided, which for example supplies or removes fluids tempered by the tempering media 28, 30 simultaneously to or from the blow moulds 1. It is likewise possible for only one fluid tempered by means of one of the tempering media 28, 30 to be capable of being supplied to the blow mould 1 through the group of switching valves 32. The group of switching valves 32 can therefore for example cause or set the supply of a fluid to a duct 6a-6d which leads to the blow mould 1. The regulating unit 32 can be actuated manually or automatically, but it is preferable in some aspects for automatic actuation to take place in a manner dependent upon specific operating parameters, such as for example the fluid temperature, the temperature of the blow mould 1, the conveying speed of the blow mould 1, the duration of the temperature and/or the like.

A two-dimensional illustration of the rotary medium distributor 23 is shown in FIG. 4. It is evident from this illustration that the rotary medium distributor 23 can be provided with a plurality of blow moulds 1 which can in some aspects be supplied with an operating fluid or a heat transfer fluid by way of at least one supply line 24a and a discharge line 24b in each case.

It will be apparent to those skilled in the art that various modifications and variations can be made to the blow mould capable of being sterilised and the methods of treating devices of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed is:

1. A method of treating devices of a plant for producing plastics material containers, with the steps:
   selecting at least one treatment device;
   acting upon the treatment device with a sterilization temperature in order to sterilize the treatment device, said acting step including
      connecting at least one tempering medium to the treatment device in a thermal manner, and
      tempering the treatment device at the sterilization temperature by way of the at least one tempering medium;
   supplying at least one plastics material pre-form to the treatment device;
   shaping the plastics material pre-form to form a plastics material container; and
   removing the at least one plastics material container from the treatment device.

2. A method according to claim 1, further comprising enclosing, at least for a time, a plastics material container in the treatment device at least in part.

3. A method according to claim 1, wherein at least one blow mould, one blowing nozzle, one stretch rod, one base mould, and/or one clamp arranged on the mould carrier for taking up the pre-form from a transfer device for the subsequent sterilization is selected as a treatment device.

4. A method according to claim 1, further comprising flowing a fluid tempered by the tempering medium around and/or through the treatment device at least locally.

5. A method according to claim 4, wherein the fluid comprises, at least in part, a water/glycol mixture, thermal oil, water, and/or the like.

6. A method according to claim 1, wherein the tempering step comprises tempering the treatment device to a sterilization temperature of at least 60° C.

7. A method according to claim 6, wherein the tempering step comprises tempering the treatment device to a sterilization temperature of at least 100° C.

8. A method according to claim 7, wherein the tempering step comprises tempering the treatment device to a sterilization temperature of at least 121° C.

9. A method according to claim 6, wherein the sterilization temperature is achieved by one of electrical heating and electromagnetic heating.

10. A method according to claim 9, wherein the sterilization temperature is achieved by means of induction.

11. A method according to claim 1, wherein the treatment device is tempered for at least 10 minutes.

12. A method according to claim 11, wherein the treatment device is tempered for at least 20 minutes.

13. A method according to claim 12, wherein the treatment device is tempered for at least 30 minutes.

14. A method according to claim 1, further comprising opening the treatment device after the sterilization in order to supply at least one container.

15. A method according to claim 1, further comprising supplying at least one disinfectant to the treatment device before and/or during the stressing with the sterilization temperature.

16. A method according to claim 1, wherein the at least one treatment device comprises the blow mould, a blowing nozzle, a stretch rod, and/or a base mould which are acted upon with the sterilization temperature.

17. A blow mould for shaping pre-forms into containers, comprising:
   at least one first part of a blow mould wall having a first inner surface and a first outer surface;
   at least one second part of a blow mould wall movable with respect to the first part, the second part having a second inner surface and a second outer surface; and
   a control apparatus designed in order to control a tempering medium for tempering the blow mould, the blow mould being capable of being brought to a specified sterilization temperature outside the actual operation,
   wherein a negative container shape is formed by the inner surface at least locally and the first and second parts of the blow mould wall are capable of being coupled to each other by means of a coupling device in order to produce a closed state, and
   wherein the tempering medium for tempering the blow mould at a sterilization temperature is arranged at least in the vicinity of at least one of the first and second parts at least for a time.

18. The blow mould according to claim 17, wherein the sterilization temperature is produced by a heating coil or coil associated with the blow mould.

* * * * *